(12) United States Patent
Hemme et al.

(10) Patent No.: US 6,773,697 B2
(45) Date of Patent: Aug. 10, 2004

(54) IRON OXIDE AND SILICON DIOXIDE-TITANIUM DIOXIDE MIXED OXIDE

(75) Inventors: Ina Hemme, Hanau (DE); Herbert Habermann, Biebergemünd (DE); Steffen Hasenzahl, Maintal (DE)

(73) Assignee: Degussa AG, Düsseldorf (DE)

( * ) Notice: Subject to any disclaimer, the term of this patent is extended or adjusted under 35 U.S.C. 154(b) by 0 days.

(21) Appl. No.: 10/314,216

(22) Filed: Dec. 9, 2002

(65) Prior Publication Data

US 2003/0124076 A1 Jul. 3, 2003

Related U.S. Application Data

(63) Continuation of application No. 09/957,651, filed on Sep. 21, 2001.

(30) Foreign Application Priority Data

Sep. 26, 2000 (EP) ............................................. 00120893

(51) Int. Cl.$^7$ .............................. A61K 7/32; A61K 7/00; A61K 7/035; A61K 33/00; A61K 33/26
(52) U.S. Cl. ........................ 424/65; 424/400; 424/401; 424/69; 424/617; 424/646; 424/724
(58) Field of Search ...................................... 424/65, 69

(56) References Cited

U.S. PATENT DOCUMENTS

| | | | |
|---|---|---|---|
| 4,297,143 A | | 10/1981 | Kleinschmit et al. |
| 4,605,554 A | * | 8/1986 | Prussin et al. ................. 424/66 |
| 5,451,390 A | | 9/1995 | Hartmann et al. |
| 5,672,330 A | | 9/1997 | Hartmann et al. |
| 5,762,914 A | | 6/1998 | Hartmann et al. |
| 6,022,404 A | | 2/2000 | Ettlinger et al. |

FOREIGN PATENT DOCUMENTS

| | | | |
|---|---|---|---|
| EP | 0 612 516 | 8/1994 | |
| EP | 0 612 516 A1 * | 8/1994 | ............ A61K/7/42 |
| EP | 0 609 533 | 10/1994 | |

OTHER PUBLICATIONS

English language abstract of OR above.

* cited by examiner

Primary Examiner—Thurman K. Page
Assistant Examiner—Simon J. Oh
(74) Attorney, Agent, or Firm—Smith, Gambrell & Russell, LLP

(57) ABSTRACT

Iron oxide-silicon dioxide-titanium dioxide mixed oxide is produced by burning vaporizable compounds of iron, silicon and titanium together in a hydrogen/oxygen flame. The mixed oxides may be used as UV absorbers in cosmetics.

8 Claims, 1 Drawing Sheet

UV Transmission of highly-disperse titanium dioxide

Figure 1:
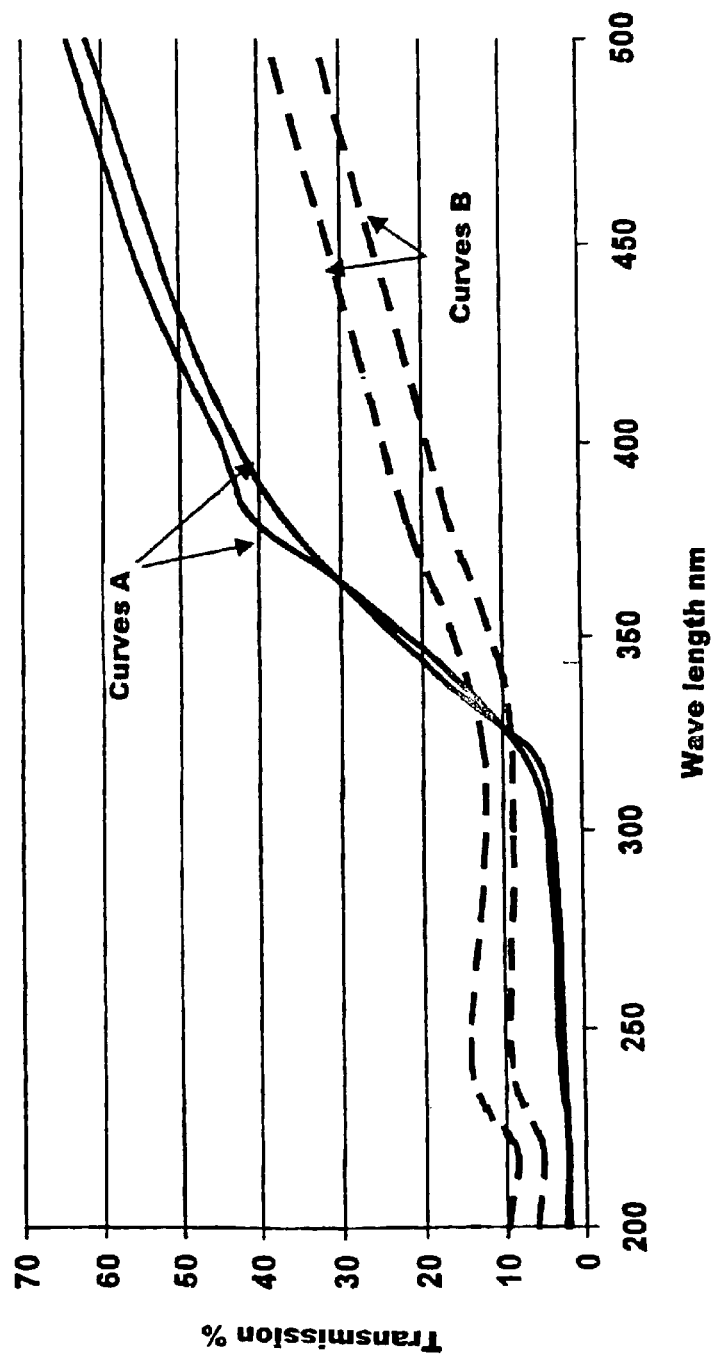

3% in IPP with 5 – 10% in aerosil 200

Layer thickness 10 μm

IRON OXIDE AND SILICON DIOXIDE-TITANIUM DIOXIDE MIXED OXIDE

CROSS-REFERENCE TO RELATED APPLICATIONS

This is a continuation of application Ser. No. 09/957,651, filed Sep. 21, 2001, the entire disclosure of which is incorporated herein by reference thereto.

The invention relates to an iron oxide-silicon dioxide-titanium dioxide mixed oxide, the process for producing it and its use.

The production of titanium dioxide by pyrogenic means, primarily by flame hydrolysis, is known (DE-PS 830 786). A titanium dioxide produced in this way can be used in sunscreens as a UV absorber which is, at the same time, transparent to visible light. It can also be used in lacquers or plastics.

The production of mixed oxides by pyrogenic means is known from the documents DE-A 952 891, DE-A 29 31 585, DE-A 24 31 810 and DE-A 36 11 449.

JP-A-5330825 discloses titanium dioxide doped with iron oxide, which is produced by precipitation and is preferably coated with further oxides.

Flame-hydrolysis can be used also to produce titanium dioxide powder containing iron oxide, as disclosed in EP 0 609 533 B1. Particular applications, such as for example as a UV absorber in sunscreens, require particularly high absorbency of UV radiation, in particular UVB radiation, and transparency, which cannot be achieved with the known titanium dioxide.

The invention provides an iron oxide-silicon dioxide-titanium dioxide mixed oxide produced pyrogenically, in particular by flame hydrolysis. It can consist of a pyrogenically, in particular flame-hydrolytically-produced ternary iron oxide-silicon dioxide-titanium dioxide mixed oxide with a specific surface of 10–200 m$^2$/g, which contains 0.5 to 50 wt. % iron oxide and 0.5–=wt. % silicon dioxide, in relation to the total quantity, as constituents of the ternary mixed oxide.

The invention further provides a process for the production of the iron oxide-silicon dioxide-titanium dioxide mixed oxide, which is characterised in that vapourable iron compounds are vapourised and transferred to the mixing chamber of a known burner, vapourable silicon compounds and titanium compounds are at the same time dosed separately and vapourised together and also transferred to the mixing chamber of the known burner, the vapourised gaseous compounds being dosed in a ratio equivalent to the composition of the iron oxide-silicon dioxide-titanium dioxide mixed oxide, the gaseous compounds are mixed in the mixing chamber of the known burner with (core) hydrogen and (core) oxygen and/or (core) air and the gas mixture which flows out of the nozzle opening of the burner is burned in the reaction chamber of the burner, (shell) hydrogen and optionally (shell) nitrogen also being fed into the ring nozzle surrounding the burner throat, the iron oxide-silicon dioxide-titanium dioxide mixed oxide formed is separated from the gaseous reaction products and optionally liberated from adhering reaction products by means of water vapour.

The iron oxide-silicon dioxide-titanium dioxide mixed oxide can be produced by vapourising anhydrous iron (III) chloride, transferring it together with an inert gas, for example nitrogen, to the mixing chamber of a known burner, mixing it there with hydrogen, air and a mixture of gaseous titanium tetrachloride and silicon tetrachloride, which is dosed separately but vapourised together, optionally with a carrier gas, which can be inert, such as for example nitrogen and/or air, in a ratio equivalent to the composition of the iron oxide-silicon dioxide-titanium dioxide mixed oxide, burning the multi-component mixture in the reaction chamber (flame tube) of the burner, (shell) hydrogen and optionally (shell) nitrogen also being fed into the ring nozzle surrounding the burner throat, then separating the solid from the gaseous reaction products and optionally liberating them from adhering reaction products in moist air.

A burner device as disclosed in the document EP 0 814 057 B1 can be used for the process according to the invention.

In a preferred embodiment the iron oxide-silicon dioxide-titanium dioxide mixed oxide may have the following physical-chemical data:

| | |
|---|---|
| Titanium dioxide content (wt. %) | 0.5–99.0 |
| Iron oxide content (wt. %) | 0.5–50 |
| Silicon dioxide content (wt. %) | 0.5–50 |
| Specific surface (m$^2$/g) | 10–200 |
| Primary particle size (nm) | 5–120 |
| Tamped density (g/l) | 100–400 |
| Ignition loss (2 h, 1000° C.) (wt. %) | 0.5–5 |
| Chloride content (wt. %) | <1 |

The iron oxide-silicon dioxide-titanium dioxide mixed oxide obtained has very fine particles and is very homogenous and very pure. It has better absorption of and thus poorer transparency to UV light combined with extensive transparency to visible light, than the prior art. It disperses easily in a particular medium, for example a sunscreen.

The iron oxide-silicon dioxide-titanium dioxide mixed oxide can also be used for the production of cosmetics, lacquers, catalysts, catalyst carriers and photocatalysts and as a UV absorber.

The invention also provides skin cosmetics which contain the iron oxide-silicon dioxide-titanium dioxide mixed oxide according to the invention, preferably in a quantity of 0.05–10 wt. %.

EXAMPLE 1

FeCl$_3$, SiCl$_4$ and TiCl$_4$ are dosed into three separate dosing devices and vapourised in two separate evaporators (evaporator temperatures 350° C. for FeCl$_3$ and 200° C. for TiCl$_4$ and SiCl$_4$). SiCl$_4$ and TiCl$_4$ are dosed separately but vapourised together in one evaporator. FeCl$_3$ is also dosed separately but is vapourised separately. The chloride vapours are directed into the mixing chamber of the burner using nitrogen. There they are mixed with (core) hydrogen and dried (core) air and/or core(oxygen) and burned in a reaction chamber (flame tube), (shell) hydrogen and optionally (shell) nitrogen is also fed into the ring nozzle surrounding the burner throat. In the coagulation stage, the iron oxide-silicon dioxide-titanium dioxide mixed oxide is cooled to about 100° C. The iron oxide-silicon dioxide-titanium dioxide mixed oxide obtained is then filtered off. Adhering chloride is removed by treating the iron oxide-silicon dioxide-titanium dioxide mixed oxide with moist air at temperatures of 500° C. to 700° C.

Table 1 lists the reaction conditions for the production of the iron oxide-silicon dioxide-titanium dioxide mixed oxide.

Table 2 shows the product characteristics of the iron oxide-silicon dioxide-titanium dioxide mixed oxide.

TABLE 1

Experimental conditions for the production of the ternary pyrogenic iron oxide-silicon dioxide-titanium dioxide mixed oxide

| Example No. | $TiCl_4$ [kg/h] | $SiCl_4$ [kg/h] | $FeCl_3$ [kg/h] | $H_2$ core [m³/h] | $H_2$ shell [m³/h] | $N_2$ core [m³/h] | $N_2$ shell [m³/h] | Primary air [m³/h] | $O_2$ core [m³/h] | Gas temp. [°C.] |
|---|---|---|---|---|---|---|---|---|---|---|
| 1 | 1.31 | 0.37 | 0.02 | 0.42 | 0.10 | 0.54 | 0.13 | 2.78 | 0.13 | 350 |

Explanatory note:
Primary air = Quantity of air in the central tube;
$H_2$ core = hydrogen in the central tube;
$H_2$ shell = shell hydrogen;
$N_2$ core = nitrogen in the central tube;
$N_2$ shell = shell nitrogen; ;
$O_2$ core = oxygen in the central tube;
Gas temp. = temperature of the gas in the nozzle of the central tube

TABLE 2

| Example No. | $TiO_2$ (%) | $SiO_2$ (%) | $Fe_2O_3$ (%) | pH (4% aqueous suspension) | Spec. surface (BET) (m²/g) | Tamped density (g/l) | Ignition loss (%) | Chloride content (%) |
|---|---|---|---|---|---|---|---|---|
| 1 | 80.07 | 18.51 | 1.35 | 3.89 | 85 | 82 | 1.07 | 0.07 |

Ignition loss (2 h at 1000° C., in accordance with DIN 55921, ASTM D 1208, JIS K 5101, in relation to the substance dried for 2 h at 105° C.); pH = pH value in 4% aqueous suspension; Tamped density in accordance with DIN/ISO 787/XI, JISK 5101/18 (not sieved)

Measurement of UV Absorption

To measure the UV absorption or transmission, 3% of the iron oxide-silicon dioxide-titanium dioxide mixed oxide according to example 1 with the composition 1.35 wt. % $Fe_2O_3$, 18.51 wt. % $SiO_2$, 80.07 wt. % $TiO_2$ is dispersed in a mixture containing 8 wt. % aerosil 200 and 89 wt. % isopropyl palmitate. The dispersion is then placed in a quartz cuvette in a layer 10 μm thick. Transmission is measured with a Shimazu UV-201 spectrometer. Pyrogenic titanium dioxide P 25 (spec. Surface 50±15 m²/g) is used as a reference substance and is investigated under the same conditions.

FIG. 1 shows the dependence of transmission on a wavelength in the range 200–400 nm, expressed in percent (Curve A: iron oxide-silicon dioxide-titanium dioxide mixed oxide according to the invention, Curve B: Titanium dioxide P 25). The dispersion containing the mixed oxide according to the invention has markedly lower transmission in the UVB range than the dispersion containing pure titanium dioxide P 25. The iron oxide-silicon dioxide-titanium dioxide mixed oxide thus offers excellent protection against UV radiation, in particular in the particularly damaging UVB range.

What is claimed is:

1. Iron oxide-silicon dioxide-titanium dioxide mixed oxide which consists of a pyrogenically-produced iron oxide-silicon dioxide-titanium dioxide mixed oxide with a specific surface of 10 to 200 m²/g, which contains 0.5 wt. % to 50 wt. % iron oxide and 0.5 wt. % to 50 wt. % of silicon dioxide in relation to the total quantity, as a constituent of the mixed oxide.

2. A method for preparing a composition suitable as a cosmetic, lacquer, catalyst, catalyst carrier, photocatalyst or UV absorber, comprising, adding to the other ingredients of the cosmetic, lacquer, catalyst, catalyst carrier, photocatalyst or UV absorber the pyrogenically-produced iron oxide-silicon dioxide-titanium dioxide mixed oxide according to claim 1.

3. Skin cosmetics containing iron oxide-silicon dioxide-titanium dioxide mixed oxide according to claim 1.

4. Skin cosmetic according to claim 3, comprising from 0.05 wt. % to 10 wt. % of the mixed oxide.

5. Iron oxide-silicon dioxide-titanium dioxide mixed oxide according to claim 1, which is produced by flame hydrolysis.

6. A method for preparing a composition suitable as a cosmetic, lacquer, catalyst, catalyst carrier, photocatalyst or UV absorber, comprising, adding to the other ingredients of the cosmetic, lacquer, catalyst, catalyst carrier, photocatalyst or UV absorber the pyrogenically-produced iron oxide-silicon dioxide-titanium dioxide mixed oxide according to claim 5.

7. Skin cosmetics containing iron oxide-silicon dioxide-titanium dioxide mixed oxide according to claim 5.

8. Iron oxide-silicon dioxide-titanium dioxide mixed oxide according to claim 5, which consists of a pyrogenically-produced iron oxide-silicon dioxide-titanium dioxide mixed oxide with a specific surface of 10 to 200 m²/g, which contains 0.5 wt. % to 50 wt. % iron oxide and 0.5 wt. % to 50 wt. % of silicon dioxide in relation to the total quantity, as a constituent of the mixed oxide.

* * * * *